US008268761B2

(12) United States Patent
Suen et al.

(10) Patent No.: US 8,268,761 B2
(45) Date of Patent: Sep. 18, 2012

(54) AMINOMETHYL-SUBSTITUTED IMIDAZOLE COMPOUNDS FOR USE AS FRICTION MODIFIERS IN LUBRICATING OIL COMPOSITIONS

(75) Inventors: Yat Fan Suen, Pinole, CA (US); Miranda L. Lackie, Richmond, CA (US); Farzan Parsinejad, Emeryville, CA (US)

(73) Assignee: Chevron Oronite Company LLC, San Ramon, CA (US)

( * ) Notice: Subject to any disclaimer, the term of this patent is extended or adjusted under 35 U.S.C. 154(b) by 332 days.

(21) Appl. No.: 12/633,581

(22) Filed: Dec. 8, 2009

(65) Prior Publication Data

US 2011/0136710 A1    Jun. 9, 2011

(51) Int. Cl.
*C10M 133/46* (2006.01)

(52) U.S. Cl. .................. 508/284; 508/283

(58) Field of Classification Search .............. 508/268, 508/283, 284; 548/300.1
See application file for complete search history.

(56) References Cited

U.S. PATENT DOCUMENTS

2009/0170734 A1    7/2009    Schwab et al.

FOREIGN PATENT DOCUMENTS

| GB | 1061904 | 3/1967 |
|----|---------|--------|
| GB | 1511593 | 5/1978 |
| JP | 09030920 A * | 2/1997 |

OTHER PUBLICATIONS

Jimenez, A.E. et al., "Room Temperature Ionic Liquids as Lubricant Additives in Steel-aluminium Contacts: Influence of Sliding Velocity, Normal Load and Temperature", Wear, 2006, vol. 261, No. 3-4, pp. 347-369, ISSN 0043-1648.
Mu, Zonggan et al., "Investigation of Tribological Behavior of Al-Si Alloy Against Steel Lubricated With Ionic Liquids of 1-Diethylphosphonyl-n-propyl-3-Alkylimidazolium Tetrafluoroborate", Journal of Tribology, 2008, vol. 130, No. 3, 034501/1-5, ISSN 0742-4787.
Qu, Jun et al., "Ionic Liquids as Novel Lubricants and Additives for Diesel Engine Applications", Tribology Letters, Sep. 2009, vol. 35, No. 3 pp. 181-189, ISSN 1023-8883.
Stocker, Fred B., Kurtz, James L., Gilman, Byron L., and Forsyth, David A., "The Mannich Reaction of Imidazoles", The Journal of Organic Chemistry, vol. 35, No. 4, Apr. 1970, pp. 883-887.
PCT International Search Report and the Written Opinion of the International Searching Authority, PCT/US2010/058883, Aug. 17, 2011.

\* cited by examiner

*Primary Examiner* — James Goloboy
*Assistant Examiner* — Taiwo Oladapo
(74) *Attorney, Agent, or Firm* — Joseph P. Foley

(57) ABSTRACT

Disclosed are aminomethyl-substituted imidazole compounds and their use as friction modifiers in lubricating oils. Also disclosed is a process for preparing the aminomethyl-substituted imidazole compounds. A further aspect is directed to a lubricating oil composition and a lubricating oil additive concentrate having the aminomethyl-substituted imidazole compounds of the present invention.

10 Claims, No Drawings

AMINOMETHYL-SUBSTITUTED IMIDAZOLE COMPOUNDS FOR USE AS FRICTION MODIFIERS IN LUBRICATING OIL COMPOSITIONS

FIELD OF THE INVENTION

The present invention generally relates to organic friction modifier compounds, more particularly to aminomethyl-substituted imidazole compounds and their use as friction modifiers in lubricating oils. Also disclosed, is a process for preparing the aminomethyl-substituted imidazole compounds as well as lubricating oil compositions containing said aminomethyl-substituted imidazole compounds and lubricating oil additive concentrate comprising the aminomethyl-substituted imidazole compounds of the present invention and a liquid organic diluent.

BACKGROUND OF THE INVENTION

In the U.S., Corporate Average Fuel Economy (CAFE) regulations mandate a specified, gradual increase of a corporate fleet's overall fuel economy by established target dates. In conjunction, industry-wide research and development has also been undertaken to improve fuel economy through new engine design and importantly through new approaches to lubricating oil formulating. Lubricant optimization is especially preferred over engine hardware changes due to its comparative lower cost per unit in fuel efficiency and possibility for backward compatibility with older engines.

Engine oil acts as a lubricant between moving engine parts at various conditions of load, speed and temperature. Hence, the various engine components experience different combinations of boundary layer, mixed and (elasto) hydrodynamic regimes of lubrication; with the largest frictional losses at piston liner/piston ring interface and a smaller part by the bearing and valve train. To reduce the energy losses due to friction of the various parts and to prevent engine wear, additives are incorporated into the engine oil such as friction modifiers, anti-wear agents, and antioxidants; the latter of which tend to lengthen the effect of the aforementioned additives. Also to reduce the hydrodynamic friction in the piston/cylinder, the viscosity of engine oils has been lowered in recent years, which has increased the dependence on friction modifiers to offset the new boundary layer regime. Organic friction modifiers are generally composed of a polar head group with hydrogen-bonding capability and a non-polar straight hydrocarbon chain for oil solubility. These friction modifiers generally operate at boundary layer conditions by forming thin mono-molecular layers of physically adsorbed polar oil-soluble products or reaction layers which can be readily sheared off and which exhibit a significantly lower friction coefficients compared to typical anti-wear or extreme pressure agents. The most commonly used organic friction modifiers are fatty acid amides, such as oleylamide, fatty amines, such as oleylamine, and fatty acid esters, such as glycerol monooleate.

To improve fuel efficiency, there has been a drive to develop new components which improve the frictional properties of the lubricating oil composition.

BACKGROUND ART

Elliott et al., GB 1,061,904 discloses and exemplifies aminomethyl derivatives of benzimidazoles and aminomethyl derivatives of benzotriazole; and their use as metal deactivators in lubricating compositions or functional fluids. Phillips et al., GB 1,511,593 discloses substituted aminomethyl hydrogenated benzimidazoles and benzotriazoles indicating their use as metal passivators in functional fluids.

SUMMARY OF THE INVENTION

The present invention is directed to aminomethyl-substituted imidazole compounds and their use as friction modifiers in lubricating oils. Thus, oil soluble aminomethyl-substituted imidazole compounds may be added to an oil of lubricating viscosity to form a lubricating oil composition having improved frictional properties. Also disclosed is a process for preparing the aminomethyl-substituted imidazole compounds through a Mannich reaction of imidazole, formaldehyde and a $C_8$ to $C_{28}$ aliphatic mono amine. A further aspect is directed to a lubricating oil additive concentrate containing a liquid organic diluents and the aminomethyl-substituted imidazole compounds of the present invention.

Accordingly, one embodiment is directed to aminomethyl-substituted imidazole compounds which can be represented by the formula I:

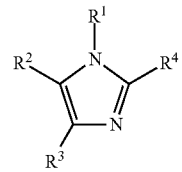

formula I wherein $R^1$, $R^2$, $R^3$ and $R^4$ are independently selected from the group consisting of hydrogen, a $C_1$ to $C_4$ alkyl group and a moiety of formula —$CH_2NHR^5$ provided that at least one $R^1$, $R^2$, $R^3$ and $R^4$ is a moiety of formula —$CH_2NHR^5$ wherein $R^5$ is a $C_8$ to $C_{28}$ aliphatic group. In this regard, the substituents are selected such that the overall compound is oil soluble; typically this is by selecting the degree of substitution, suitable chain length or chain branching in the aliphatic group. In a further aspect, $R^1$, $R^2$ and $R^4$ are hydrogen and $R^3$ is of formula —$CH_2NHR^5$ wherein $R^5$ is a $C_{10}$ to $C_{28}$ aliphatic group. Preferred aliphatic groups are $C_8$ to $C_{28}$ alkyl and alkenyl groups either branched or straight chain groups. Thus in one aspect the aliphatic groups are alkenyl groups. More particularly the aliphatic groups saturated aliphatic groups. Particularly preferred are mono and di-substituted aminomethyl groups and accordingly another aspect is directed to compound of the formula II:

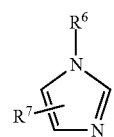

formula II wherein $R^6$ and $R^7$ are independently selected from the group consisting of hydrogen, a $C_1$ to $C_4$ alkyl group and a moiety of formula —$CH_2NHR^8$ provided that at least one $R^6$ and $R^7$ is a moiety of formula —$CH_2NHR^8$ wherein $R^8$ is a $C_8$ to $C_{28}$ aliphatic group. In another aspect $R^8$ is a $C_{10}$ to $C_{18}$ aliphatic group. Preferred aliphatic groups are alkyl and alkenyl groups, either straight or branched chain; more preferred are saturated aliphatic groups. In one aspect the aliphatic group is a linear saturated aliphatic group. The aliphatic group is selected so that the overall compound is rendered oil soluble.

Mono aminomethyl substituents are directed to when $R^6$ is hydrogen or when $R^7$ is hydrogen. Typically the compound of formula II will exist as mixtures due to the method for preparation of the compounds; and mixtures are typically employed in the lubricating compositions. Carbon attachment of —$CH_2NHR^8$ group on the imidazole can be directed where $R^6$ is selected to from $C_1$ to $C_4$ alkyl group. In this aspect, for carbon attachment of —$CH_2NHR^8$ group the 4 and 5 position of the imidazole are preferred.

A further embodiment of the present invention is directed to processes for preparing aminomethyl-substituted imidazoles which comprises reacting (a) an imidazole compound having the formula III

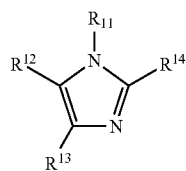

formula III wherein $R^{11}$, $R^{12}$, $R^{13}$ and $R^{14}$ are independently selected from the group consisting of hydrogen and a $C_1$ to $C_4$ alkyl group wherein at least one of $R^{11}$, $R^{12}$, $R^{13}$ and $R^{14}$ is hydrogen;

(b) formaldehyde or a formaldehyde-producing reagent; and (c) an amine of having the formula

$H_2N—R^{15}$ wherein $R^{15}$ is a $C_8$ to $C_{28}$ aliphatic group. Particularly suited aliphatic groups are $C_{10}$ to $C_{28}$ aliphatic group and more preferably a $C_{10}$ to $C_{18}$ aliphatic group. In one aspect the aliphatic group is a saturated aliphatic group. Preferred amines include decylamine, dodecylamine, hexadecylamine, oleylamine, and octadecylamine.

A further embodiment of the present invention is directed to a lubricating oil composition comprising a major amount of an oil of lubricating viscosity and from 0.01 to 5 weight percent of one or more of the above described aminomethyl-substituted imidazoles of the present invention.

A further embodiment of the present invention is directed to a lubricating oil additive concentrate comprising 10 percent to 90 weight percent of a liquid organic diluent and from about 90 to 10 weight percent of one or more of the above described aminomethyl-substituted imidazoles of the present invention. Both the lubricating oil composition and the lubricating oil additive concentrate may contain other additives designed to improve the properties of the lubricating oil.

DETAILED DESCRIPTION OF THE INVENTION

As used herein, the following terms have the following meaning unless expressly stated to the contrary:

The term "aliphatic" as used herein refers to both branched and straight chain hydrocarbon groups, which are saturated or unsaturated. In other words, the aliphatic group may be alkyl, alkenyl or alkynyl.

The term "alkyl" as used herein refers to both branched and straight chain saturated aliphatic hydrocarbon groups, and where specified, having the specified number of carbon atoms. Thus, the term "$C_1$ to $C_4$ alkyl," as used herein, indicates an alkyl group having from 1 to 4 carbon atoms such as methyl, ethyl, n-propyl, isopropyl, n-butyl, sec-butyl and tert-butyl.

The term "alkenyl" as used herein refers to branched or straight hydrocarbon chains comprising one or more unsaturated carbon-carbon bonds.

The term "alkynyl" as used herein refers to branched or straight hydrocarbon chains comprising one or more triple carbon-carbon bonds.

Processes for Preparing Aminomethyl-Substituted Imidazole Compounds

Aminomethyl-substituted imidazole compounds of the present invention may be prepared by numerous reaction mechanisms; employing either a multi-step process or a single step process.

Thus, one process for preparing the aminomethyl-substituted imidazole compounds comprises:

(a) reacting (i) at least one imidazole carboxaldehyde of formula IV

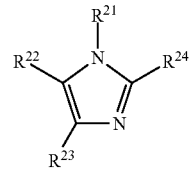

formula IV wherein $R^{21}$, $R^{22}$, $R^{23}$ and $R^{24}$ are independently selected from the group consisting of hydrogen, a $C_1$ to $C_4$ alkyl group and a moiety of formula —COH provided that at least one $R^{21}$, $R^{22}$, $R^{23}$ and $R^{24}$ is a moiety of formula —COH; and (ii) a primary amine having the formula $H_2N—R^{25}$ wherein $R^{25}$ is a $C_8$ to $C_{28}$ aliphatic group; and (b) reducing the reaction product of (a) with a hydrogen source.

Some examples of imidazole carboxaldehydes of formula IV contemplated for use in the preparation of aminomethyl-substituted imidazoles include 1H-imidazole-1-carboxaldehyde, imidazole-2-carboxaldehyde, imidazole-4-carboxaldehyde, 1-methyl-2-imidazolecarboxaldehyde, and 1-methyl-5-imidazolecarboxaldehyde. Imidazole dicarboxaldehydes and imidazole trioxaldehydes may also be employed Amines contemplated for use in this process have the following formula:

$H_2N—R^{25}$ wherein $R^{25}$ is a $C_8$ to $C_{28}$ aliphatic group, preferably a $C_{10}$ to $C_{28}$ aliphatic group and more preferably, $R^{25}$ is a $C_{10}$ to $C_{18}$ aliphatic group. Preferred amines include decylamine, dodecylamine, hexadecylamine, oleylamine, and octadecylamine A hydrogen source is employed to reduce the reaction product of step (a). Any suitable hydrogen source that is capable of reducing the imine formed in step (a) may be used. Preferred hydrogen sources include lithium aluminum hydride, sodium borohydride, and hydrogen gas in combination with a catalyst such as palladium on carbon.

Aminomethyl-substituted imidazole compounds of the present invention may also be prepared in a single step process using conventional methods for the preparation of Mannich reaction products. Methods for preparing Mannich reaction products of imidazoles are disclosed by Stocker, F. B. et al., J. Org. Chem. 1970, 35, 883-887. In a preferred embodiment of the present invention, the process for preparing the aminomethyl-substituted imidazole compounds comprises, reacting:

(a) an imidazole compound having the formula III

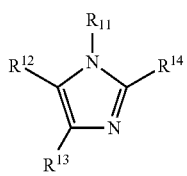

formula III wherein $R^{11}$, $R^{12}$, $R^{13}$ and $R^{14}$ are independently selected from the group consisting of hydrogen and a $C_1$ to $C_4$ alkyl group wherein at least one of $R^{11}$, $R^{12}$, $R^{13}$ and $R^{14}$ is hydrogen;

(b) formaldehyde or a formaldehyde-producing reagent; and (c) an amine of having the formula

wherein $R^{15}$ is a $C_8$ to $C_{28}$ aliphatic group. Particularly suited aliphatic groups are $C_{10}$ to $C_{28}$ aliphatic group and more preferably a $C_{10}$ to $C_{18}$ aliphatic group. The aliphatic groups is selected to impart oil solubility for the component, alkyl and alkenyl groups are preferred and may include straight chain and branched chain. In one aspect the aliphatic group is a saturated aliphatic group. Preferred amines include octylamine, decylamine, dodecylamine, tetradecylamine, hexadecylamine, octadecylamine and oleylamine; branched amines include 2-ethylhexylamine, isotridecylamine, 2-butyloctylamine, 2-hexyldecylamine, 2-octyldodecylamine and the like. A particularly preferred branched amine is 2-ethylhexylamine A particularly preferred alkenyl amine is oleylamine Some examples of imidazole compounds contemplated for use in the preparation of aminomethyl-substituted imidazoles of the present invention include imidazole, 1-methylimidazole, 2-methylimidazole, 4-methylimidazole, 2-ethylimidazole, 2-ethyl-4-methylimidazole, 2-propylimidazole and 2-isopropylimidazole. As illustrated by the imidazole of formula III there are four possible site of reaction on the imidazole. Preferably at least two of $R^{11}$, $R^{12}$, $R^{13}$ and $R^{14}$ are hydrogen and in another aspect three of $R^{11}$, $R^{12}$, $R^{13}$ and $R^{14}$ are selected to be hydrogen. Imidazoles unsubstituted at the 1 position are expected to readily undergo the Mannich reaction under conventional conditions, for C-substitution $R^{12}$ and $R^{13}$ are expected to be more reactive and thus preferred to be unsubstituted.

Formaldehyde or Formaldehyde-Producing Reagent

By formaldehyde is meant all its forms, including gaseous, liquid and solid. Formaldehyde-producing reagents include paraformaldehyde and aqueous formaldehyde solutions such as formalin. Examples of gaseous formaldehyde is the monomer $CH_2O$ and the trimer, $(CH_2O)_3$ (trioxane), having the formula given below:

Examples of liquid formaldehyde are the following:
(a) monomer $CH_2O$ in ethyl ether
(b) monomer $CH_2O$ in water which has the formulas $CH_2(H_2O)_2$ (methylene glycol) and $HO(CH_2O)_nH$
(c) monomer $CH_2O$ in methanol which has the formulas $OHCH_2OCH_3$ and $CH_3O(CH_2O)_nH$.

Formaldehyde solutions are commercially available in water and various alcohols. In water it is available as a 37%-50% solution. Formalin is a 37% solution in water. Formaldehyde is also commercially available as linear and cyclic (trioxane) polymers. Linear polymers may be low molecular weight or high molecular weight polymers.

The relative quantities of imidazole, formaldehyde and amine will be determined by the nature of the desired final product. If a monosubstituted Mannich reaction product is desired, the imidazole starting material, the amine starting material and the formaldehyde should be used in approximately equimolar amounts. As another example, if a disubstituted Mannich reaction product is desired, then about two mole equivalents of formaldehyde and about two mole equivalents of amine should be used per mole of imidazole starting material; and the like. Mixtures of amines may be employed. Conventional methods are employed in the Mannich reaction. A particular aspect is directed to the primarily monosubstituted Mannich reaction product, using the above named reactants in the respective molar ratios of imidazole, amine and aldehyde of approximately 1:0.1-2:0.1-2. Preferably, the respective molar ratios will be 1:0.5-1.5:0.5-1.5. More preferably, the respective molar ratios will be 1:0.8-1.3: 0.8-1.3. For more substituted Mannich reaction products clearly the ratio of amine and aldehyde would be increased.

The reaction is preferably conducted at atmospheric pressure although subatmospheric pressures and/or superatmospheric pressures may be used, if desired. Normally, the reaction is normally conducted at a temperature within the range of about 10° C. to about 200° C., preferably from about 20° C. to about 120° C. however for more substituted imidazoles are used, it may be necessary to use higher temperatures and/or pressures, such as temperatures within the range of about 100° C. to about 150° C. and pressures within the range of about 1 atmosphere to about 50 atmospheres.

The present invention is also directed to a lubricating oil composition comprising a major amount of a base oil of lubricating viscosity and a minor amount of one or more of the above described the aminomethyl-substituted imidazole derivatives of the present invention. Typically the aminomethyl-substituted imidazole compound or mixtures thereof is incorporated in the lubricating oil composition in an amount from 0.01 to 5 weight percent, more preferably from 0.1 to 2.5 weight percent and furthermore from 0.25 to 1 weight percent of the aminomethyl-substituted imidazole based upon the total lubricating oil composition.

The base oil of lubricating viscosity for use in the lubricating oil compositions of this invention is typically present in a major amount, e.g., an amount of greater than 50 weight percent, preferably greater than about 70 weight percent, more preferably from about 80 to about 99.5 weight percent and most preferably from about 85 to about 98 weight percent, based on the total weight of the composition. The expression "base oil" as used herein shall be understood to mean a base stock or blend of base stocks which is a lubricant component that is produced by a single manufacturer to the same specifications (independent of feed source or manufacturer's location); that meets the same manufacturer's specification; and that is identified by a unique formula, product identification number, or both. The base oil for use herein can be any presently known or later-discovered base oil of lubricating viscosity used in formulating lubricating oil compositions for any and all such applications, e.g., engine oils, marine cylinder oils, functional fluids such as hydraulic oils, gear oils, transmission fluids, etc.

As one skilled in the art would readily appreciate, the viscosity of the base oil is dependent upon the application. Accordingly, the viscosity of a base oil for use herein will ordinarily range from about 2 to about 2000 centistokes (cSt) at 100° Centigrade (C). Generally, individually the base oils used as engine oils will have a kinematic viscosity range at 100° C. of about 2 cSt to about 30 cSt, preferably about 3 cSt to about 16 cSt, and most preferably about 4 cSt to about 12 cSt and will be selected or blended depending on the desired end use and the additives in the finished oil to give the desired grade of engine oil, e.g., a lubricating oil composition having an SAE Viscosity Grade of 0W, 0W-20, 0W-30, 0W-40, 0W-50, 0W-60, 5W, 5W-20, 5W-30, 5W-40, 5W-50, 5W-60, 10W, 10W-20, 10W-30, 10W-40, 10W-50, 15W, 15W-20, 15W-30 or 15W-40. Oils used as gear oils can have viscosities ranging from about 2 cSt to about 2000 cSt at 100° C.

Base stocks may be manufactured using a variety of different processes including, but not limited to, distillation, solvent refining, hydrogen processing, oligomerization, esterification, and rerefining. Rerefined stock shall be substantially free from materials introduced through manufacturing, contamination, or previous use. The base oil of the lubricating oil compositions of this invention may be any natural or synthetic lubricating base oil. Suitable hydrocarbon synthetic oils include, but are not limited to, oils prepared from the polymerization of ethylene or from the polymerization of 1-olefins to provide polymers such as polyalphaolefin or PAO oils, or from hydrocarbon synthesis procedures using carbon monoxide and hydrogen gases such as in a Fischer-Tropsch process. For example, a suitable base oil is one that comprises little, if any, heavy fraction; e.g., little, if any, lube oil fraction of viscosity 20 cSt or higher at 100° C.

The base oil may be derived from natural lubricating oils, synthetic lubricating oils or mixtures thereof. Suitable base oil includes base stocks obtained by isomerization of synthetic wax and slack wax, as well as hydrocracked base stocks produced by hydrocracking (rather than solvent extracting) the aromatic and polar components of the crude. Suitable base oils include those in all API categories I, II, III, IV and V as defined in API Publication 1509, 14th Edition, Addendum I, Dec. 1998. Group IV base oils are polyalphaolefins (PAO). Group V base oils include all other base oils not included in Group I, II, III, or IV.

Useful natural oils include mineral lubricating oils such as, for example, liquid petroleum oils, solvent-treated or acid-treated mineral lubricating oils of the paraffinic, naphthenic or mixed paraffinic-naphthenic types, oils derived from coal or shale, animal oils, vegetable oils (e.g., rapeseed oils, castor oils and lard oil), and the like.

Useful synthetic lubricating oils include, but are not limited to, hydrocarbon oils and halo-substituted hydrocarbon oils such as polymerized and interpolymerized olefins, e.g., polybutylenes, polypropylenes, propylene-isobutylene copolymers, chlorinated polybutylenes, poly(1-hexenes), poly(1-octenes), poly(1-decenes), and the like and mixtures thereof; alkylbenzenes such as dodecylbenzenes, tetradecylbenzenes, dinonylbenzenes, di(2-ethylhexyl)-benzenes, and the like; polyphenyls such as biphenyls, terphenyls, alkylated polyphenyls, and the like; alkylated diphenyl ethers and alkylated diphenyl sulfides and the derivative, analogs and homologs thereof and the like.

Other useful synthetic lubricating oils include, but are not limited to, oils made by polymerizing olefins of less than 5 carbon atoms such as ethylene, propylene, butylenes, isobutene, pentene, and mixtures thereof Methods of preparing such polymer oils are well known to those skilled in the art.

Additional useful synthetic hydrocarbon oils include liquid polymers of alpha-olefins having the proper viscosity. Especially useful synthetic hydrocarbon oils are the hydrogenated liquid oligomers of $C_6$ to $C_{12}$ alpha-olefins such as, for example, 1-decene trimer.

Another class of useful synthetic lubricating oils include, but are not limited to, alkylene oxide polymers, i.e., homopolymers, interpolymers, and derivatives thereof where the terminal hydroxyl groups have been modified by, for example, esterification or etherification. These oils are exemplified by the oils prepared through polymerization of ethylene oxide or propylene oxide, the alkyl and phenyl ethers of these polyoxyalkylene polymers (e.g., methyl polypropylene glycol ether having an average molecular weight of 1,000, diphenyl ether of polyethylene glycol having a molecular weight of 500-1000, diethyl ether of polypropylene glycol having a molecular weight of 1,000-1,500, etc.) or mono- and polycarboxylic esters thereof such as, for example, the acetic esters, mixed $C_3$-$C_8$ fatty acid esters, or the $C_{13}$ oxo acid diester of tetraethylene glycol.

Yet another class of useful synthetic lubricating oils include, but are not limited to, the esters of dicarboxylic acids e.g., phthalic acid, succinic acid, alkyl succinic acids, alkenyl succinic acids, maleic acid, azelaic acid, suberic acid, sebacic acid, fumaric acid, adipic acid, linoleic acid dimer, malonic acids, alkyl malonic acids, alkenyl malonic acids, etc., with a variety of alcohols, e.g., butyl alcohol, hexyl alcohol, dodecyl alcohol, 2-ethylhexyl alcohol, ethylene glycol, diethylene glycol monoether, propylene glycol, etc. Specific examples of these esters include dibutyl adipate, di(2-ethylhexyl)sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethylhexanoic acid and the like.

Esters useful as synthetic oils also include, but are not limited to, those made from carboxylic acids having from about 5 to about 12 carbon atoms with alcohols, e.g., methanol, ethanol, etc., polyols and polyol ethers such as neopentyl glycol, trimethylol propane, pentaerythritol, dipentaerythritol, tripentaerythritol, and the like.

Silicon-based oils such as, for example, polyalkyl-, polyaryl-, polyalkoxy- or polyaryloxy-siloxane oils and silicate oils, comprise another useful class of synthetic lubricating oils. Specific examples of these include, but are not limited to, tetraethyl silicate, tetra-isopropyl silicate, tetra-(2-ethylhexyl) silicate, tetra-(4-methylhexyl)silicate, tetra-(p-tert-butylphenyl)silicate, hexyl-(4-methyl-2-pentoxy)disiloxane, poly(methyl)siloxanes, poly(methylphenyl)siloxanes, and the like. Still yet other useful synthetic lubricating oils include, but are not limited to, liquid esters of phosphorous containing acids, e.g., tricresyl phosphate, trioctyl phosphate, diethyl ester of decane phosphionic acid, etc., polymeric tetrahydrofurans and the like.

The lubricating oil may be derived from unrefined, refined and rerefined oils, either natural, synthetic or mixtures of two or more of any of these of the type disclosed hereinabove. Unrefined oils are those obtained directly from a natural or synthetic source (e.g., coal, shale, or tar sands bitumen) without further purification or treatment. Examples of unrefined oils include, but are not limited to, a shale oil obtained directly from retorting operations, a petroleum oil obtained directly from distillation or an ester oil obtained directly from an esterification process, each of which is then used without further treatment. Refined oils are similar to the unrefined oils except they have been further treated in one or more purification steps to improve one or more properties. These purification techniques are known to those of skill in the art and include, for example, solvent extractions, secondary distillation, acid or base extraction, filtration, percolation, hydrotreating, dewaxing, etc. Rerefined oils are obtained by treating used oils in processes similar to those used to obtain refined oils. Such rerefined oils are also known as reclaimed or reprocessed oils and often are additionally processed by techniques directed to removal of spent additives and oil breakdown products.

Lubricating oil base stocks derived from the hydroisomerization of wax may also be used, either alone or in combination with the aforesaid natural and/or synthetic base stocks. Such wax isomerate oil is produced by the hydroisomerization of natural or synthetic waxes or mixtures thereof over a hydroisomerization catalyst.

Natural waxes are typically the slack waxes recovered by the solvent dewaxing of mineral oils; synthetic waxes are typically the wax produced by the Fischer-Tropsch process.

The following additive components are examples of components that can be favorably employed in combination with the lubricating additive of the present invention. These examples of additives are provided to illustrate the present invention, but they are not intended to limit it.

(A) Metal Detergents: sulfurized or unsulfurized alkyl or alkenyl phenates, alkyl or alkenyl aromatic sulfonates, calcium sulfonates, sulfurized or unsulfurized metal salts of alkyl or alkenyl hydroxybenzoates, sulfurized or unsulfurized metal salts of multi-hydroxy alkyl or alkenyl aromatic compounds, alkyl or alkenyl hydroxy aromatic sulfonates, sulfurized or unsulfurized alkyl or alkenyl naphthenates, metal salts of alkanoic acids, metal salts of an alkyl or alkenyl multi-acid, and chemical and physical mixtures thereof.

(B) Ashless Dispersants: alkenyl succinimides, alkenyl succinimides modified with other organic compounds, and alkenyl succinimides modified with boric acid, alkenyl succinic ester.

(C) Oxidation Inhibitors:

(1) Phenol type oxidation inhibitors: 4,4'-methylenebis(2, 6-di-tert-butylphenol), 4,4'-bis(2,6-di-tert-butylphenol), 4,4'-bis(2-methyl-6-tert-butylphenol), 2,2'-methylenebis(4-methyl-6-tert-butyl-phenol), 4,4'-butylidenebis(3-methyl-6-tert-butylphenol), 4,4'-isopropylidenebis(2,6-di-tert-butylphenol), 2,2'-methylenebis(4-methyl-6-nonylphenol), 2,2'-isobutylidene-bis(4,6-dimethylphenol), 2,2'-methylenebis(4-methyl-6-cyclohexylphenol), 2,6-di-tert-butyl-4-methylphenol, 2,6-di-tert-butyl-4-ethylphenol, 2,4-dimethyl-6-tert-butyl-phenol, 2,6-di-tert-α-dimethylamino-p-cresol, 2,6-di-tert-4(N.N' dimethylaminomethylphenol), 4,4'-thiobis(2-methyl-6-tert-butylphenol), 2,2'-thiobis(4-methyl-6-tert-butylphenol), bis(3-methyl-4-hydroxy-5-tert-butylbenzyl)sulfide, and bis(3,5-di-tert-butyl-4-hydroxybenzyl)sulfide.

(2) Diphenylamine type oxidation inhibitor: alkylated diphenylamine, phenyl-α-naphthylamine, and alkylated α-naphthylamine (3) Other types: metal dithiocarbamate (e.g., zinc dithiocarbamate), and methylenebis(dibutyldithiocarbamate).

(D) Rust Inhibitors:

(1) Non ionic polyoxyethylene surface active agents: polyoxyethylene lauryl ether, polyoxyethylene higher alcohol ether, polyoxyethylene nonylphenyl ether, polyoxyethylene octylphenyl ether, polyoxyethylene octyl stearyl ether, polyoxyethylene oleyl ether, polyoxyethylene sorbitol monostearate, polyoxyethylene sorbitol monooleate, and polyethylene glycol monooleate.

(2) Other compounds: stearic acid and other fatty acids, dicarboxylic acids, metal soaps, fatty acid amine salts, metal salts of heavy sulfonic acid, partial carboxylic acid ester of polyhydric alcohol, and phosphoric ester.

(E) Demulsifiers: addition product of alkylphenol and ethylene oxide, polyoxyethylene alkyl ether, and polyoxyethylene sorbitane ester.

(F) Extreme Pressure Agents (EP agents): zinc dialkyldithiophosphate (ZnDTP, primary alkyl type & secondary alkyl type), sulfurized oils, diphenyl sulfide, methyl trichlorostearate, chlorinated naphthalene, benzyl iodide, fluoroalkylpolysiloxane, and lead naphthenate.

(G) Friction Modifiers: fatty alcohol, fatty acid, amine, borated ester, and other esters.

(H) Multifunctional Additives: sulfurized oxymolybdenum dithiocarbamate, sulfurized oxymolybdenum organo phosphorodithioate, oxymolybdenum monoglyceride, oxymolybdenum diethylate amide, amine-molybdenum complex compound, and sulfur-containing molybdenum complex compound (I) Viscosity Index Improvers: polymethacrylate type polymers, ethylene-propylene copolymers, styrene-isoprene copolymers, hydrated styrene-isoprene copolymers, polyisobutylene, and dispersant type viscosity index improvers.

(J) Pour-point Depressants: polymethyl methacrylate.

(K) Foam Inhibitors: alkyl methacrylate polymers and dimethyl silicone polymers.

Each of the foregoing additives, when used, is used at a functionally effective amount to impart the desired properties to the lubricant. Thus, for example, if an additive is an antioxidant, a functionally effective amount of this antioxidant would be an amount sufficient to impart the desired antioxidancy characteristics to the lubricant. Generally, the concentration of each of these additives, when used, ranges from about 0.001 to about 20 weight percent, and in one embodiment from about 0.01 to about 10 weight percent based on the total weight of the lubricating oil composition.

The present invention is also directed to a lubricating oil additive concentrate in which the additive of the present invention is incorporated into a substantially inert, normally liquid organic diluent such as, for example, mineral oil, naphtha, benzene, toluene or xylene to form an additive concentrate. Typically, a neutral oil having a viscosity of about 4 to about 8.5 cSt at 100° C. and preferably about 4 to about 6 cSt at 100° C. will be used as the diluent, though synthetic oils, as well as other organic liquids which are compatible with the additives and finished lubricating oil can also be used. Generally, the lubricating oil additive concentrate will contain 90 to 10 weight percent of an organic diluent and from about 10 to 90 weight percent of one or more additives of the present invention.

The invention is further illustrated by the following examples, which set forth particularly advantageous method embodiments. While the examples are provided to illustrate the present invention, they are not intended to limit it.

EXAMPLES

Example 1

Preparation of Decyl-(1H-imidazol-4-ylmethyl)-amine

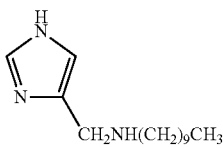

A 500 mL flask under a nitrogen atmosphere was charged with anhydrous methanol (150 mL), imidazole-4-carboxaldehyde (45.82 grams, 476 mmol) and decylamine (74.99 grams, 476 mmol) with stirring. Several drops of concentrated hydrochloric acid were added to the mixture and the mixture was allowed to reflux overnight under nitrogen. The mixture was taken up into ethyl acetate, washed with water and brine, dried with sodium sulfate, and evaporated to dryness. The crude product was dissolved in a 4:1 ratio of anhydrous THF and anhydrous MeOH and transferred to a hydrogenation reaction flask. To this solution was added 5 wt. % Pd/C (5 wt. %) and the resulting mixture was hydrogenated overnight at 30 psi $H_2$. After hydrogenation was complete, the solution was filtered through Celite under vacuum to remove the Pd/C and the filtrate was evaporated to dryness. $^1$H NMR (CDCl$_3$) δ 7.5-7.6 (1H), 6.8-6.9 (1H), 3.6-3.8 (2H), 2.6 (t, 2H), 1.5 (t, 2H), 1.2-1.4 (m, 14H), 0.8-0.9 (t, 3H).

Example 2

Preparation of Dodecyl-(1H-imidazol-4-ylmethyl)-amine

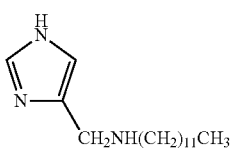

This compound was prepared according to the procedure described in Example 1 except that dodecylamine was used as the amine. $^1$H NMR (CDCl$_3$) δ 7.5-7.6 (1H), 6.8-6.9 (1H), 3.4-3.6 (2H), 2.65 (t, 2H), 1.4-1.6 (t, 2H), 1.2-1.4 (m, 18H), 0.8-0.9 (t, 3H)

Example 3

Preparation of Hexadecyl-(1H-imidazol-4-ylmethyl)-amine

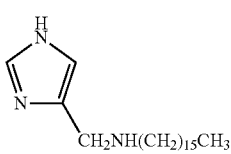

This compound was prepared according to the procedure described in Example 1 except that hexadecylamine was used as the amine $^1$H NMR (CDCl$_3$) δ 7.5-7.6 (1H), 6.8-6.9 (1H), 3.4-3.6 (2H), 2.65 (t, 2H), 1.4-1.6 (t, 2H), 1.2-1.4 (m, 26H), 0.8-0.9 (t, 3H)

Evaluation of Friction Performance

Example 4

A baseline formulation was prepared and used for assessing the frictional properties of aminomethyl-substituted imidazoles of the present invention. The baseline composition contained:
(a) 4 wt. % of a succinimide dispersant;
(b) 3.5 mM/kg of a low overbased calcium sulfonate;
(c) 45 mM/kg of a high overbased calcium sulfonate;
(d) 5 mM/kg of a secondary zinc dithiophosphate derived from a mixture of secondary alcohols;
(e) 2.0 mM/kg of a zinc dithiophosphate derived from a primary alcohol;
(f) 1.2 wt. % of a diarylamine antioxidant;
(g) 0.3 wt. % of a pour point depressant;
(h) 10 ppm Si of a foam inhibitor;
(i) 4.8 wt. % of an ethylene-propylene VII; and
(j) the balance, a Group II base oil.

The lubricating oil compositions presented in the examples were 5W-20 oils (SAE viscosity grade).

Example A (Comparative)

A lubricating oil composition was prepared by top-treating the baseline formulation of Example 4 with 0.5 wt. % of a molybdenum complex. The molybdenum complex does not function as a friction modifier.

Example B (Comparative)

A lubricating oil composition was prepared by top-treating the baseline formulation of Example 4 with 0.5 wt. % of a molybdenum complex and with 0.5 wt. % of glycerol monooleate.

Example 5

A lubricating oil composition was prepared by top-treating the baseline formulation of Example 4 with 0.5 wt. % of a molybdenum complex and with 0.5 wt. % of the aminomethyl-substituted imidazole of Example 1.

Example 6

A lubricating oil composition was prepared by top-treating the baseline formulation of Example 4 with 0.5 wt. % of a molybdenum complex and with 0.5 wt. % of the aminomethyl-substituted imidazole of Example 2.

Example 7

A lubricating oil composition was prepared by top-treating the baseline formulation of Example 4 with 0.5 wt. % of a molybdenum complex and with 0.5 wt. % of the aminomethyl-substituted imidazole of Example 3.

The compositions described above were tested for friction performance in a Mini-Traction Machine (MTM) bench test. The MTM is manufactured by PCS Instruments and operates with a ball (0.75 inches 8620 steel ball) loaded against a rotating disk (32100 steel). The conditions employ a load of approximately 10-30 Newtons, a speed of approximately 10-2000 mm/s and a temperature of approximately 125-150° C. In this bench test, friction performance is measured as the comparison of the total area between the first Stribeck curve generated with the baseline formulation and the second Stribeck curve generated with the baseline formulation top-treated with a molybdenum complex and with a friction modifier. Lower total area values correspond to better friction performance of the oil. The results of this evaluation are set forth in the Table 1 below:

TABLE 1

|  | Friction Modifier | Stribeck Area |
|---|---|---|
| Comp. Ex A | — | 140 |
| Comp. Ex. B | Glycerol monooleate | 80 |
| Example 5 | Imidazole of Ex. 1 | 60 |
| Example 6 | Imidazole of Ex. 2 | 73 |
| Example 7 | Imidazole of Ex. 3 | 72 |

The bench test results demonstrate comparable friction performance of the aminomethyl-substituted imidazoles of the present invention with glycerol monooleate, a standard organic friction modifier used in lubricating oil compositions.

Evaluation of Fuel Economy Benefit

The fuel economy performance of lubricating oil compositions containing different organic friction modifiers was evaluated. A V-6 2.5 L engine was adjusted to run at a rotational speed of 1400 r/min and a temperature of about 107 to about 120° C. Three high detergent oil flushes were first run through the engine for twenty minutes each. The engine was then operated for two hours and then thirty grams of a mixture containing the engine lubricating oil composition top-treated with 0.5 wt. % of the organic friction modifier was added to the engine through a specially adapted oil fill cap. The engine was allowed to stabilize for two hours.

The torque (power) was evaluated by averaging the torque for a period of one hour prior to addition of the friction modifier top-treat and averaging the torque for a period of two hours immediately following the addition of the friction modifier top-treat. Results are reported as the percent change in torque from one hour before addition of the friction modifier top-treat to two hours after addition of the friction modifier. Results are reported as an average of two runs. A higher percent of torque increase corresponds to higher fuel economy benefit. The results of this evaluation are set forth in the Table 2 below:

TABLE 2

| Friction Modifier Top-Treat | % Torque Increase |
|---|---|
| Imidazole of Ex. 1 | 1.48 |
| Glycerol monooleate | 1.18 |
| Oleylamine | 0.94 |

As the results indicate, the lubricating oil composition containing an aminomethyl-substituted imidazole of the present invention gave superior improvement in fuel economy relative to lubricating oil compositions containing standard organic friction modifiers glycerol monooleate or oleylamine.

What is claimed is:

1. A compound of formula I:

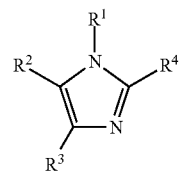

formula I wherein $R^1$, $R^2$ and $R^4$ are hydrogen; and $R^3$ is a moiety of formula —$CH_2NHR^5$ wherein $R^5$ is a $C_{10}$ to $C_{28}$ aliphatic group.

2. The compound of claim 1 wherein $R^5$ is $C_{10}$ to $C_{18}$ aliphatic group.

3. A compound having the formula:

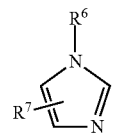

wherein $R^6$ and is a moiety of formula —$CH_2NHR^8$ wherein $R^8$ is a $C_8$ to $C_{28}$ aliphatic group and $R^7$ is hydrogen.

4. A lubricating oil composition comprising a major amount of an oil of lubricating viscosity and from 0.01 to 5 weight percent of one or more compounds having the formula

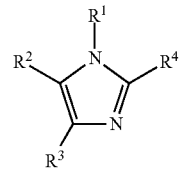

wherein $R^1$, $R^2$, $R^3$ and $R^4$ are independently selected from the group consisting of hydrogen, a $C_1$ to $C_4$ alkyl group and a moiety of formula —$CH_2NHR^5$ provided that at least one $R^1$, $R^2$, $R^3$ and $R^4$ is a moiety of formula —$CH_2NHR^5$ wherein $R^5$ is a $C_8$ to $C_{28}$ aliphatic group.

5. The lubricating oil composition of claim 4 wherein $R^1$, $R^2$ and $R^4$ are hydrogen and $R^3$ is a moiety of formula —$CH_2NHR^5$ wherein $R^5$ is a $C_{10}$ to $C_{28}$ aliphatic group.

6. The lubricating oil composition of claim 4 wherein $R^5$ is a $C_{10}$ to $C_{18}$ aliphatic group.

7. A lubricating oil additive concentrate comprising from 90 to 10 weight percent of a liquid organic diluent and from about 10 to 90 weight percent of one or more compounds having the formula

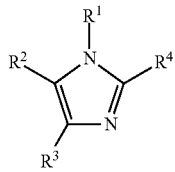

wherein $R^1$, $R^2$, $R^3$ and $R^4$ are independently selected from the group consisting of hydrogen, a $C_1$ to $C_4$ alkyl group and a moiety of formula —$CH_2NHR^5$ provided that at least one $R^1$, $R^2$, $R^3$ and $R^4$ is a moiety of formula —$CH_2NHR^5$ wherein $R^5$ is a $C_8$ to $C_{28}$ aliphatic group.

8. The lubricating oil additive concentrate of claim 7 wherein $R^1$, $R^2$ and $R^4$ are hydrogen and $R^3$ is a moiety of formula —$CH_2NHR^5$ wherein $R^5$ is a $C_{10}$ to $C_{28}$ aliphatic group.

9. A compound having the formula:

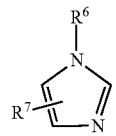

wherein: $R^6$ is a $C_1$ to $C_4$ alkyl group; and $R^7$ is a moiety of formula —$CH_2NHR^8$ wherein $R^8$ is a $C_8$ to $C_{28}$ aliphatic group.

10. The compound of claim 9 wherein $R^7$ is substituted in the 4 or 5 position of the imidazole ring.

* * * * *